(12) United States Patent
Asogawa et al.

(10) Patent No.: US 10,139,134 B2
(45) Date of Patent: Nov. 27, 2018

(54) SAMPLE HEATING METHOD AND HEATING CONTROL DEVICE

(75) Inventors: Minoru Asogawa, Tokyo (JP); Hisashi Hagiwara, Kanagawa (JP)

(73) Assignee: NEC CORPORATION, Tokyo (JP)

( * ) Notice: Subject to any disclaimer, the term of this patent is extended or adjusted under 35 U.S.C. 154(b) by 1274 days.

(21) Appl. No.: 13/996,949

(22) PCT Filed: Dec. 19, 2011

(86) PCT No.: PCT/JP2011/007064
§ 371 (c)(1),
(2), (4) Date: Jun. 21, 2013

(87) PCT Pub. No.: WO2012/086168
PCT Pub. Date: Jun. 28, 2012

(65) Prior Publication Data
US 2013/0273487 A1 Oct. 17, 2013

(30) Foreign Application Priority Data
Dec. 21, 2010 (JP) .................................. 2010-284217

(51) Int. Cl.
*F24H 9/20* (2006.01)
*B01L 3/00* (2006.01)
*B01L 7/00* (2006.01)
*G01N 35/00* (2006.01)

(52) U.S. Cl.
CPC .............. *F24H 9/20* (2013.01); *B01L 3/5027* (2013.01); *B01L 3/52* (2013.01); *B01L 7/52* (2013.01); *B01L 2200/0684* (2013.01); *B01L 2200/142* (2013.01); *B01L 2300/0816* (2013.01); *B01L 2300/14* (2013.01); *B01L 2300/18* (2013.01); *B01L 2300/1805* (2013.01); *B01L 2300/1822* (2013.01); *B01L 2400/0481* (2013.01); *G01N 2035/00356* (2013.01)

(58) Field of Classification Search
USPC .................. 422/501; 435/91.2, 283.1, 287.2
See application file for complete search history.

(56) References Cited

U.S. PATENT DOCUMENTS 8,008,091 B2 * 8/2011 Higashino ............. B01F 5/0646
422/500
2005/0153430 A1 7/2005 Ohtaka
2006/0019379 A1 * 1/2006 Taylor .................... C12M 47/06
435/306.1

(Continued)

FOREIGN PATENT DOCUMENTS

EP 2071026 A1 6/2009
JP 2006-262788 A 10/2006
(Continued)

OTHER PUBLICATIONS

Machine translation of JP2007-278789 of Inoue Masao (Inventor).*
(Continued)

*Primary Examiner* — Joseph M Pelham

(57) ABSTRACT

A microchip includes a vessel portion, an elastic member, and a flow channel which leads a liquid sample to the vessel portion. After a liquid sample is put in the vessel portion, the liquid sample is heated while pressure is applied with respect to an inner portion of the vessel portion.

10 Claims, 13 Drawing Sheets

(56) References Cited

U.S. PATENT DOCUMENTS

| | | | | |
|---|---|---|---|---|
| 2008/0262213 | A1* | 10/2008 | Wu | B01F 5/0646 |
| | | | | 536/25.4 |
| 2009/0023201 | A1 | 1/2009 | Hongo et al. | |
| 2010/0056383 | A1* | 3/2010 | Ririe | B01L 3/50273 |
| | | | | 506/7 |
| 2010/0221814 | A1 | 9/2010 | Asogawa et al. | |
| 2010/0317093 | A1* | 12/2010 | Turewicz | B01L 3/50273 |
| | | | | 435/287.2 |
| 2010/0323432 | A1* | 12/2010 | Asogawa | B01F 11/0071 |
| | | | | 435/287.2 |
| 2011/0039305 | A1* | 2/2011 | Termaat | B01L 7/52 |
| | | | | 435/91.2 |
| 2011/0053289 | A1* | 3/2011 | Lowe | B01L 3/5027 |
| | | | | 436/501 |
| 2013/0137172 | A1* | 5/2013 | Ririe | C12M 33/00 |
| | | | | 435/306.1 |
| 2013/0263940 | A1* | 10/2013 | Weber | B01L 3/50 |
| | | | | 137/340 |

FOREIGN PATENT DOCUMENTS

| | | |
|---|---|---|
| JP | 2007-278789 A | 10/2007 |
| WO | 2009/038203 A1 | 3/2009 |

OTHER PUBLICATIONS

International Search Report for PCT Application No. PCT/JP2011/007064, dated Feb. 7, 2012.

Extended European Search Report for EP Application No. EP11851156.7 dated on Aug. 10, 2016.

* cited by examiner

SAMPLE HEATING METHOD AND HEATING CONTROL DEVICE

This application is a National Stage Entry of PCT/JP2011/007064 filed Dec. 19, 2011, which claims priority from Japanese Patent Application 2010-284217 filed Dec. 21, 2010, the contents of all of which are incorporated herein by reference, in their entirety.

TECHNICAL FIELD

The present invention relates to a sample heating method which uses a microchip, and a heating control device using the method.

BACKGROUND ART

In recent years, a "micro channel device" has been known which includes a microstructure such as a micro channel (flow channel) and a port in a substrate. As a technology of this kind, there is a technology disclosed in Patent Document 1.

In Patent Document 1, a microchip is described which includes, between two stacked elastic plates, a portion which is bonded to each other and a portion which is not bonded to each other and in which the non-bonded portion becomes a vessel portion and an inflow channel. In the microchip, the vessel portion is expanded like a balloon, a sample of a predetermined small amount is filled in the inner portion of the vessel portion, and thereafter, the vessel portion is sealed, and the sample is heated.

RELATED DOCUMENT

Patent Document

[Patent Document 1] Pamphlet of International Publication WO 2009/038203

SUMMARY OF THE INVENTION

Problems to be Solved by the Invention

However, in the technology disclosed in Patent Document 1, according to the knowledge of the inventors, it is clear that if the sealed vessel portion is continuously heated, solvent in the small sample amount in the vessel portion is evaporated according to the lapse of time and permeates the elastic plates. Thereby, according to a decrease of enzyme activity due to change of pH or the like, efficiency in a reaction using a biological sample, such as an amplification reaction of DNA, is decreased. Moreover, the sample in the vessel portion is solidified, and thus, there is also a problem in that the sample cannot be discharged from the vessel portion.

The present invention is made in consideration of the above-described circumstances, and an object thereof is to provide a sample heating method which uses a microchip capable of heating the sample while preventing the vaporization of a solvent or a dispersion medium in a small liquid sample amount.

BRIEF SUMMARY OF THE INVENTION

According to the present invention, there is provided a sample heating method which uses a microchip, wherein the microchip includes:

a vessel portion in which at least a portion is configured of an elastic member; and a flow channel which leads a liquid sample to the vessel portion, and wherein the liquid sample is heated while pressure is applied with respect to an inner portion of the vessel portion in which the liquid sample is put.

In addition, according to the present invention, there is provided a heating control device including:

a heating unit which heats a vessel portion in which at least a portion is configured of an elastic member and a liquid sample put in the vessel portion of a microchip which includes a flow channel leading the liquid sample to the vessel portion;

a pressure applying unit which applies pressure with respect to an inner portion of the vessel portion; and a control unit which controls a heating by the heating unit and a pressure applying by the pressure applying unit so as to heat the liquid sample while applying pressure with respect to the inner portion of the vessel portion.

Advantageous Effects of the Invention

According to the present invention, it is possible to heat the sample while preventing vaporization of solvent or a dispersion medium in a small liquid sample amount.

Moreover, in the present invention, the configuration is adopted in which the liquid sample is heated in a state where the liquid sample closely contacts either the heat generation member or the heat transfer member. Thereby, it is possible to decrease thermal resistance by decreasing contact thermal resistance. Therefore, a desired heat can be applied with respect to the sample which is put in the vessel portion.

BRIEF DESCRIPTION OF THE DRAWINGS

The above-described object, other objects, characteristics, and advantages are more obvious from preferred exemplary embodiments described below and the accompanying drawings below.

DESCRIPTION OF EXEMPLARY EMBODIMENTS

Figure 1:
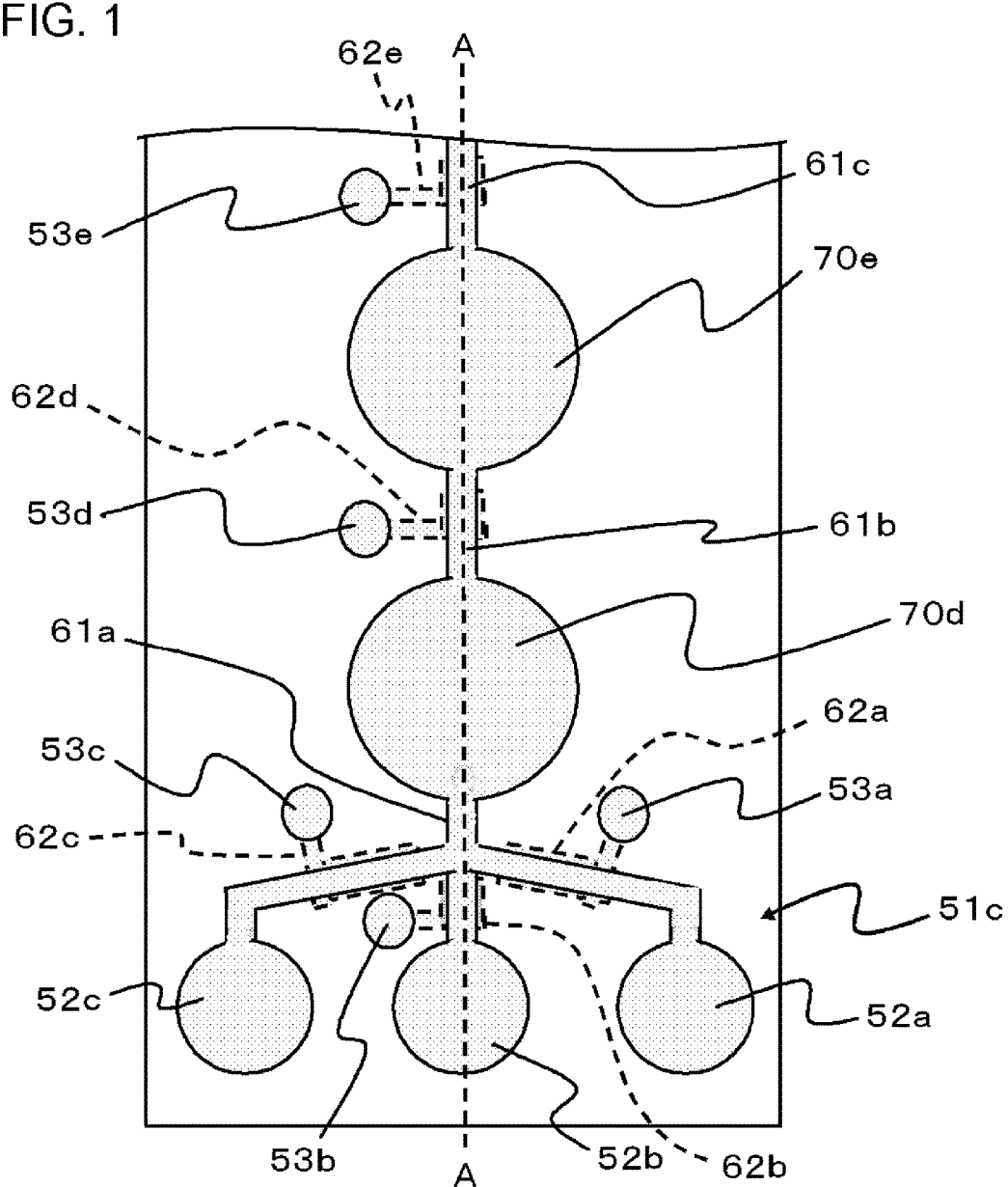
FIG. 1 is a plan view schematically showing a configuration of a second film of a microchip which is used in the first and second exemplary embodiments.

Hereinafter, exemplary embodiments of the present invention will be described with reference to drawings. Moreover, in all drawings, the same reference numerals are attached to the same components, and the descriptions will not be repeated.

First Exemplary Embodiment

The present exemplary embodiment is a sample heating method, using a microchip which includes a vessel portion in which at least a portion is configured of an elastic member a flow channel which leads a liquid sample to the vessel portion, and after putting the liquid sample in the vessel portion heating the liquid sample while applying pressure with respect to an inner portion of the vessel portion.

In the present exemplary embodiment, the microchip that may be used includes an expansion limiting member which is provided around the vessel portion and can limit expansion of an elastic member. At least a portion of the expansion limiting member may be configured of a heat transfer member. In addition, a heat generation member is formed at a side opposite to the vessel portion through the heat transfer member with respect to the vessel portion, and the liquid sample is heated in a state where the vessel portion closely contacts the heat transfer member by applying pressure with respect to the inner portion of the vessel portion. Thereby, since it is possible to decrease thermal resistance by decreasing contact thermal resistance, a desired heat can be applied with respect to the sample which is put in the vessel portion. Moreover, the contact thermal resistance can be constantly controlled by further applying pressure to the inner portion of the vessel portion through the flow channel in the state where the vessel portion closely contacts the heat transfer member. In addition, by controlling the thermal conductivity and the thickness of the heat transfer member, thermal resistivity can be further decreased. Therefore, a heating efficiency of the sample is increased, and thus, a precise temperature control is possible.

Moreover, in the present exemplary embodiment, at least a portion of the expansion limiting member may be configured of a heat generation member. In the present invention, by applying pressure with respect to the inner portion of the vessel portion using the microchip configured as described above, the liquid sample can be heated in a state where the vessel portion closely contacts the heat generation member. Accordingly, the contact thermal resistance can be decreased, and the vessel portion can be heated directly. Thereby, the thermal resistivity can be further decreased, and a more precise temperature control is possible.

Moreover, in the present exemplary embodiment, it is preferable that the entire expansion limiting member be configured of the heat generation member or the heat transfer member. By applying pressure with respect to the inner portion of the vessel portion through the flow channel using the microchip, the liquid sample can be heated in the state where the entire vessel portion closely contacts the expansion limiting member. Accordingly, the entire vessel portion is heated, and the contact thermal resistance can be decreased. Therefore, the thermal resistivity can be further decreased, and a more precise temperature control can be realized.

Moreover, in the present exemplary embodiment, a concave portion is provided in the expansion limiting member, and the liquid sample may be heated in a state where at least a portion of the expanded vessel portion closely contacts the concave portion. Accordingly, since the expansion of the vessel portion configured of the elastic member can be a constant amount, capacity of the vessel portion can be set to a desired amount.

Figure 3:
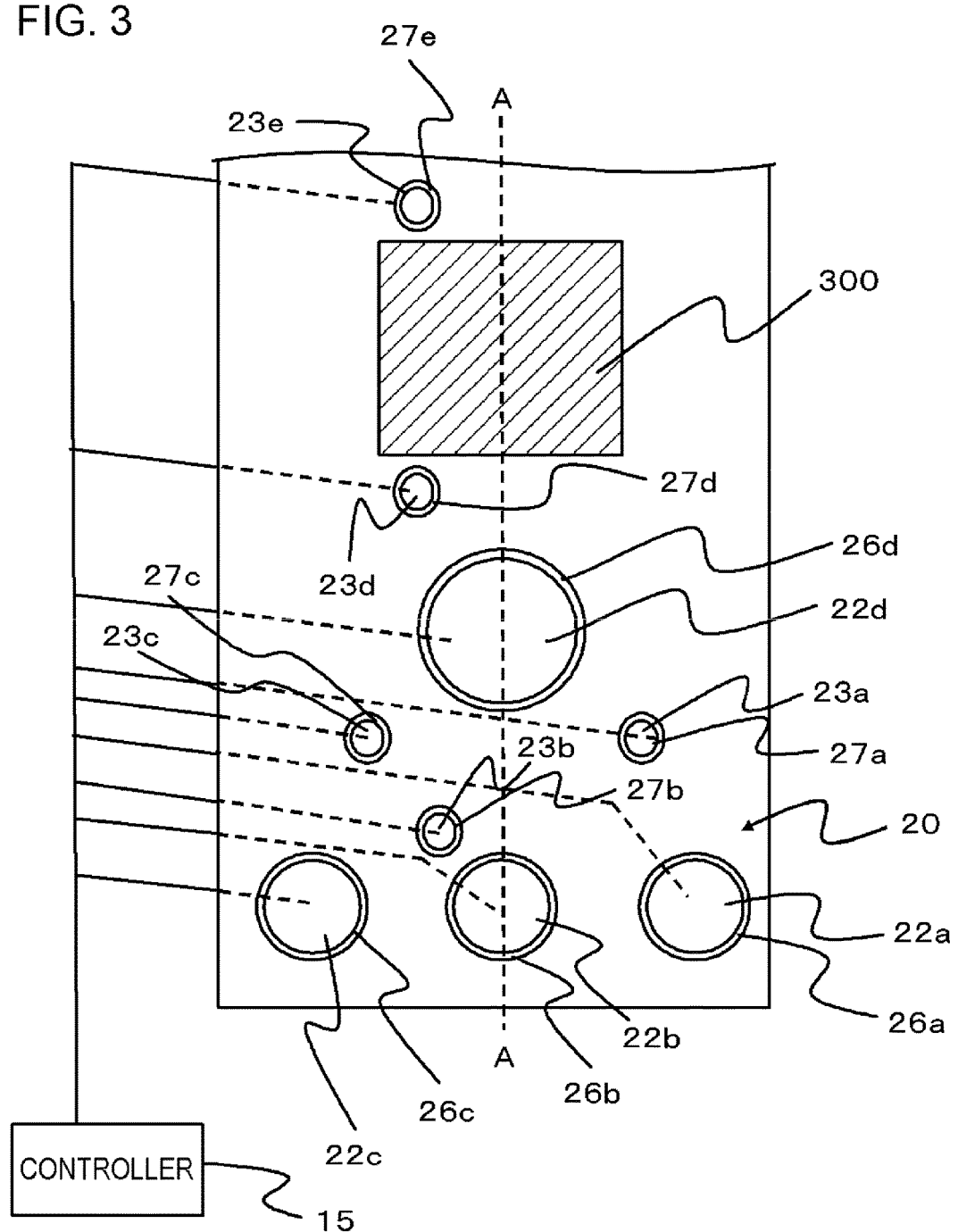
FIG. 3 is a plan view schematically showing a configuration of a cover of the microchip which is used in the first and second exemplary embodiments.
Figure 5:
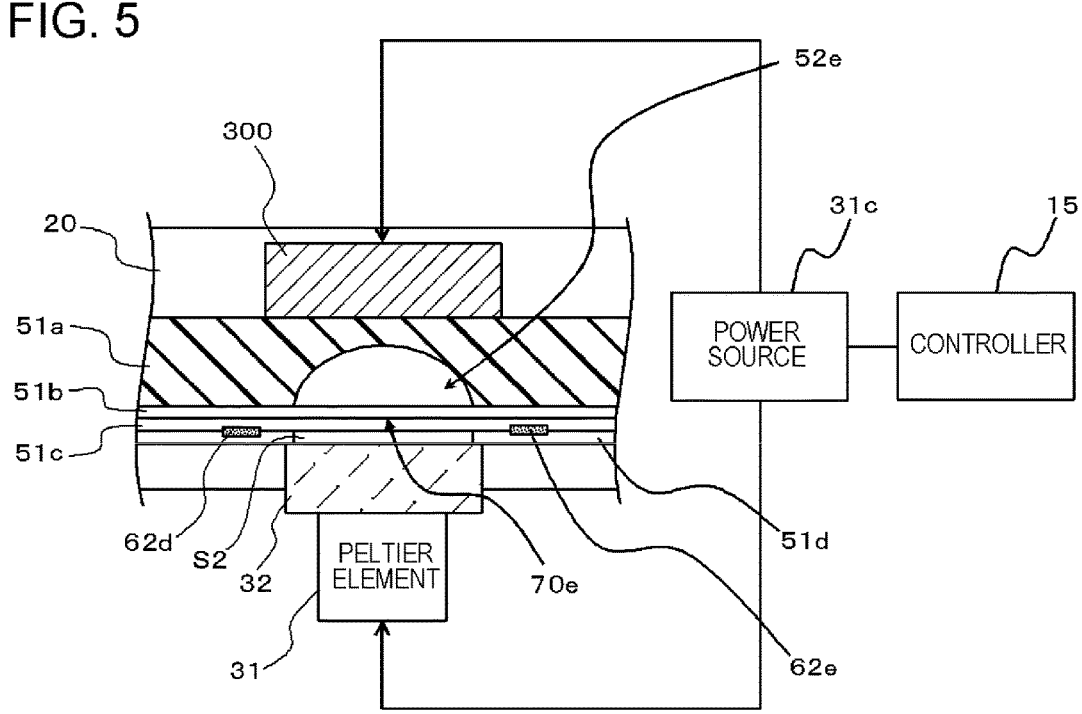
FIG. 5 is a view illustrating a temperature control mechanism of the microchip which is used in the first exemplary embodiment.

Moreover, in the sample heating method of the present exemplary embodiment, a controller 15 may be used as shown in FIGS. 3 and 5. The controller 15 is described in detail below and performs control so as to heat the liquid sample while pressure is applied to the inner portion of the vessel portion. Moreover, by using the controller, temperature of the heat generation member can be controlled. In this way, by controlling the pressure which is applied to the inner portion of the vessel portion and the heating temperature of the sample, the contact thermal resistance is controlled and a precise temperature control is possible.

Hereinafter, the present exemplary embodiment is described specifically by an example which performs amplification reaction (Polymerase Chain Reaction; PCR) of DNA by heating the liquid sample which includes DNA using the microchip.

Figure 4:
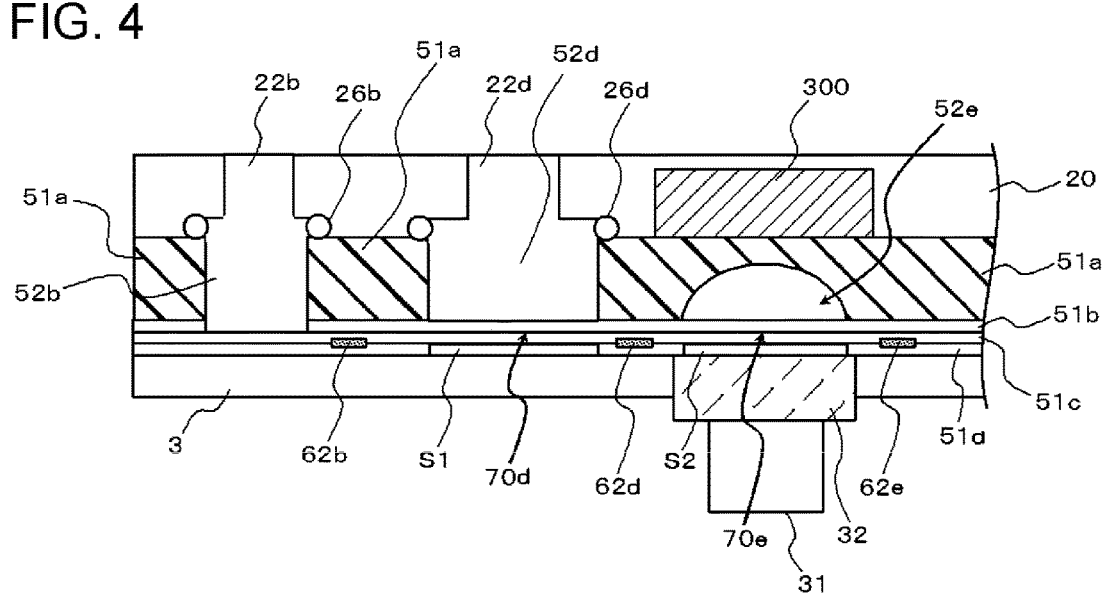
FIG. 4 is an example of a cross-sectional view taken along line A-A in the microchip shown in FIGS. 1 to 3.

As shown in FIG. 4, the microchip used in the present exemplary embodiment has a multilayer structure, and has a configuration in which a first film 51b (first elastic member) configured of a film-like elastic member, a second film 51c (second elastic member), and a third film 51d are adhered on a plate-like substrate 51a configured of a plate-like elastic member. The first film 51b and the second film 51c are adhered to each other around the vessel portion and the flow channel, and thus, the flow channel and the vessel portion are formed in a gap between the first film 51b and the second film 51c respectively. For example, selection of a specific material and a manufacturing method thereof can be appropriately selected from those disclosed in Japanese Unexamined Patent Publication No. 2007-309868. For example, as materials of the first, the second, and the third films 51b, 51c, and 51d, a silicon rubber (for example, polydimethylsiloxane (PDMS) or the like) may be exemplified. In addition, for example, as the method which forms the flow channel or the vessel portion on the bonding surface of the first film 51b and the second film 51c, there is a method by casting a silicon rubber or the like in a mold manufactured using a photolithography method in which a resist is exposed as a mask.

FIG. 1 is a plan view schematically showing a configuration of the second film 51c. In FIG. 1, a surface on which the second film 51c contacts the first film 51b is shown. Between the first film 51b and the second film 51c, a portion adhered to each other and a portion which is not adhered to each other are provided. A region, in which the shape is shown by a solid line in FIG. 1 and the inner portion is painted out, is the portion which is not bonded to the first film 51b in the second film 51c. By the non-bonded portion, a reagent tank 52a, a reagent tank 52b, a reagent tank 52c, an elastic vessel portion 70d, an elastic vessel portion 70e, a flow channel 61a, a flow channel 61b, and if necessary, a flow channel 61c are formed. For example, in the dimensions of the elastic vessel portions 70d and 70e, the diameters may be 3 mm to 5 mm, the heights may be 0.7 mm to 1 mm, and it is preferable that the elastic vessel portions be configured so as to store the liquid sample of a range of 2 µL to 10 µL.

Moreover, also between the second film 51c and the third film 51d, a portion bonded to each other and a portion which is not bonded to each other are provided. A region, in which the shape is shown by a dashed line in FIG. 1 and the inner portion is painted out, is the portion which is provided on the lower surface of the second film 51c and is not bonded between the second film 51c and the third film 51d. A pressurizing medium such as air is flowed into the non-bonded portion between the second film 51c and the third film 51d, and the non-bonded portion becomes a shutter flow channel 62a, a shutter flow channel 62b, a shutter flow channel 62c, a shutter flow channel 62d, and a shutter flow channel 62e which make the non-bonded portion between the first film 51b and the second film 51c closely contact each other. Moreover, since the pressurizing medium is flowed into each of the shutter flow channel 62a, the shutter 62b, the shutter flow channel 62c, the shutter flow channel 62d, and the shutter flow channel 62e, a shutter port 53a, a shutter port 53b, a shutter port 53c, a shutter port 53d, and a shutter port 53e, penetrating the plate-like substrate 51a, the first film 51b, and the second film 51c, are provided respectively.

Figure 2:
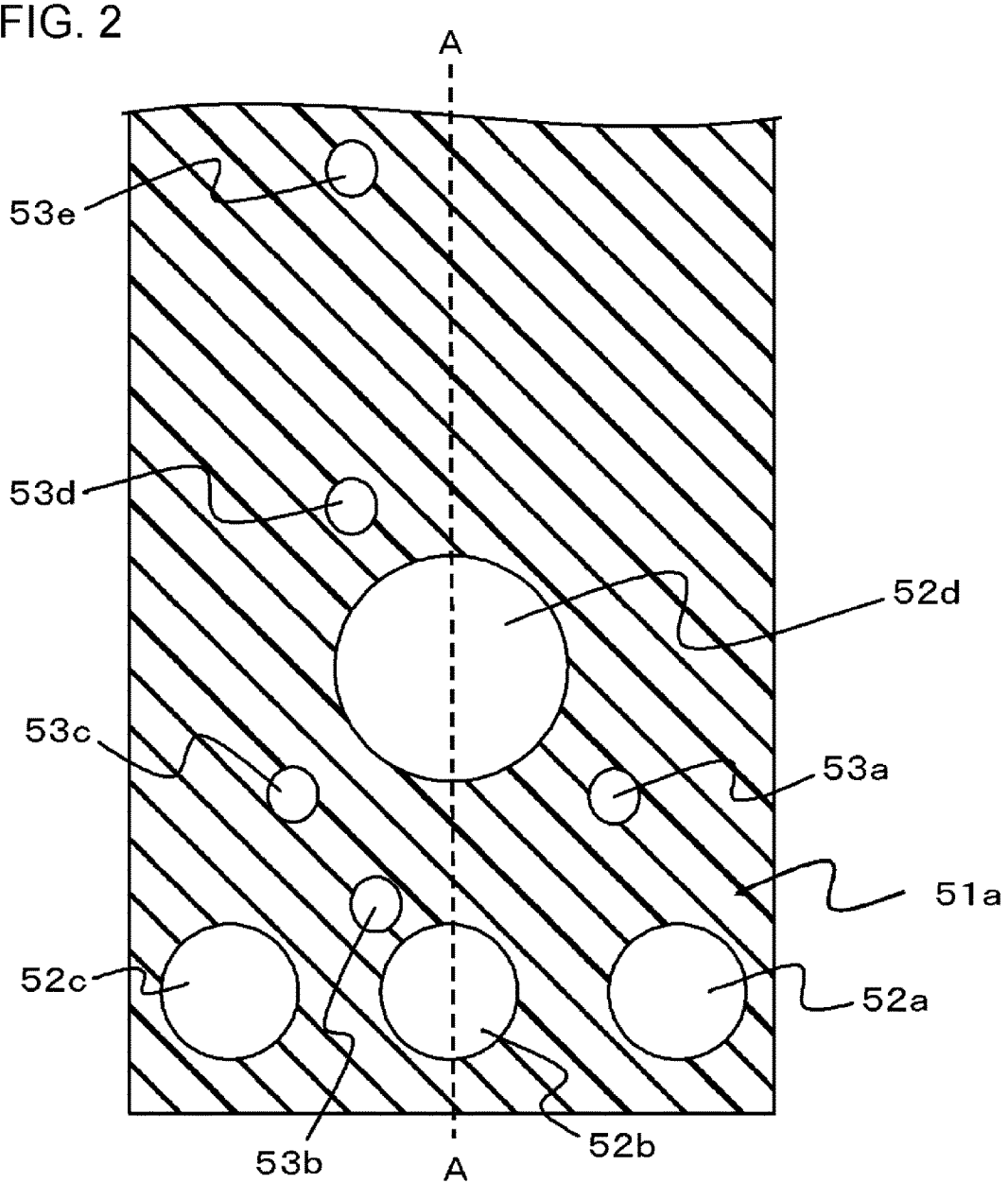
FIG. 2 is a plan view schematically showing a configuration of a plate-like substrate of the microchip which is used in the first and second exemplary embodiments.

FIG. 2 is a plan view schematically showing a configuration of the plate-like substrate 51a of the microchip according to the present exemplary embodiment. Although the details are described below, the reagent tank 52a, the reagent tank 52b, and the reagent tank 52c penetrate the plate-like substrate 51a and the first film 51b respectively. A mixing vessel 52d which penetrates the plate-like substrate 51a is provided on the upper portion of the elastic vessel portion 70d. On other hand, a through hole which penetrates the plate-like substrate 51a is not provided on the upper portion of the elastic vessel portion 70e.

Moreover, FIG. 3 is a plan view schematically showing a surface opposite to the plate-like substrate 51a in a cover 20 which is mounted on the plate-like substrate 51a. In the cover 20, a pressurizing hole 22a, a pressurizing hole 22b, a pressurizing hole 22c, and a pressurizing hole 22d, penetrating the cover, are provided respectively on positions corresponding to the reagent tank 52a, the reagent tank 52b, the reagent tank 52c, and the mixing vessel 52d. The peripheries of the pressurizing hole 22a, the pressurizing hole 22b, the pressurizing hole 22c, and the pressurizing hole 22d are sealed by an O-ring 26a, an O-ring 26b, an O-ring 26c, and an O-ring 26d respectively. Moreover, a shutter pressurizing hole 23a, a shutter pressurizing hole 23b, a shutter pressurizing hole 23c, a shutter pressurizing hole 23d, and a shutter pressurizing hole 23e are provided respectively at positions corresponding to the shutter port 53a, the shutter port 53b, the shutter port 53c, the shutter port 53d, and the shutter port 53e, and, an O-ring 27a, an O-ring 27b, an O-ring 27c, an O-ring 27d, and an O-ring 27e seals around the holes respectively. A heater 300 having a larger size than the expanded elastic vessel portion 70e when seen in a plan view is provided at a position corresponding to the upper portion of the elastic vessel portion 70e.

In the present exemplary embodiment, according to a heating control device shown in FIG. 5, heating of the elastic vessel portion 70e and applying pressure with respect to the inner portion of the elastic vessel portion 70e can be controlled. The heating control device includes a heating unit which heats the liquid sample put in the elastic vessel portion 70e, a pressure applying unit (not shown in the drawings) which applies pressure with respect to the inner portion of the elastic vessel portion 70e, and a controller (control unit) which controls the heating unit and the pressure applying unit. Although the details are described below, the heating unit is configured of a peltier element 31, a heater 300 and, a power source 31c. In addition, a voltage is applied by the power source 31c, and thus, the peltier element 31 and the heater 300 generate heat, the heat is conducted to the plate-like member 51a and the heat transfer member 32, and the liquid sample put in the elastic vessel portion 70e is heated. The controller 15 performs an applying voltage to the power source 31c and a pressure applying by above the pressure applying unit, and controls performing of preset programs so as to heat the liquid sample while applying pressure with respect to the inner portion of the elastic vessel portion 70e.

Hereinafter, the pressure applying unit not shown in the drawings will be specifically described. First, an electromagnetic valve of a drive unit is connected to the controller 15 so that the operation of the valve is controlled. Moreover, a motor, which drives a pump so as to control pressure in a pressure accumulator to a predetermined pressure, and a pressure sensor, which detects the pressure in the pressure accumulator and performs feedback, are connected to the controller 15.

In addition, the pressurizing hole 22a, the pressurizing hole 22b, the pressurizing hole 22c, the pressurizing hole 22d, the shutter pressurizing hole 23a, the shutter pressurizing hole 23b, the shutter pressurizing hole 23c, the shutter pressurizing hole 23d, and the shutter pressurizing hole 23e shown in FIG. 3 are connected to a secondary side of the drive unit, which is configured of the plurality of electromagnetic valves, through a plurality of tubes respectively, and a primary side of the electromagnetic valve is connected to the pressure accumulator. The pump which is driven by the motor and the pressure sensor which detects the inner portion pressure are connected to the pressure accumulator.

For the above-described configuration, the pressure applying unit is operated as follows. First, the pressure in the pressure accumulator is always maintained to a predetermined pressure by a command from the controller 15. Moreover, the electromagnetic valve in the drive unit is driven according to the preset programs, and the pressurizing medium stored in the pressure accumulator is flowed into the pressurizing hole 22a, the pressurizing hole 22b, the pressurizing hole 22c, the pressurizing hole 22d, the shutter pressurizing hole 23a, the shutter pressurizing hole 23b, the shutter pressurizing hole 23c, the shutter pressurizing hole 23d, and the shutter pressurizing hole 23e respectively. As the pressurizing medium, air or inert gas such as nitrogen or argon may be used. Moreover, manually without using the controller 15, the pressurizing medium is flowed into the pressurizing hole 22a, the pressurizing hole 22b, the pressurizing hole 22c, the pressurizing hole 22d, the shutter pressurizing hole 23a, the shutter pressurizing hole 23b, the shutter pressurizing hole 23c, the shutter pressurizing hole 23d, and the shutter pressurizing hole 23e respectively, and the pressure control and opening and closing of the shutter flow channel may be performed.

Referring to FIG. 4, the configuration of the microchip used in the present exemplary embodiment will be described more specifically. FIG. 4 is an example of a cross-sectional view taken along line A-A in the microchip shown in FIGS. 1 to 3. FIG. 4 shows a state before the sample is filled in the reagent tank 52a, the reagent tank 52b, the reagent tank 52c, the elastic vessel portion 70d, and the elastic vessel portion 70e.

As shown in FIG. 4, the microchip used in the present exemplary embodiment is interposed and held through the O-ring 26b and the O-ring 26d between a table 3 and the cover 20. Moreover, the elastic vessel portion 70d and the elastic vessel portion 70e are provided in a gap between the first film 51b and the second film 51c respectively. In addition, the shutter flow channel 62b, the shutter flow channel 62d, and the shutter flow channel 62e are provided in a gap between the second film 51c and the third film 51d respectively. The reagent tank 52b is provided so as to penetrate the plate-like substrate 51a and the first film 51b. The mixing vessel 52d which penetrates the plate-like substrate 51a is provided on the upper portion of the elastic vessel portion 70d. A through hole is provided in the third film 51d. Thereby, a gap portion S1 is interposed between the second film 51c which configures a portion of the elastic vessel portion 70d and the table 3, and a gap portion S2 is interposed between the third film 51d which configures a portion of the elastic vessel portion 70e and the upper surface of the heat transfer member 32 which is flush with the upper surface of the table 3. For explanation, the shutter flow channel 62b, the shutter flow channel 62d and the shutter flow channel 62e are indicated as a portion having substance. However, in the state shown in FIG. 4, substantially, the flow channels are a state of 0 in the volume. Moreover, in FIGS. 5 to 13 described below, the case where the shutter flow channel 62b, the shutter flow channel 63d, and the shutter flow channel 62e are shown by the shapes similar to the FIG. 4 substantially shows the state of 0 in the volume.

Here, in the microchip used in the present exemplary embodiment, the plate-like substrate 51a (upper substrate) and the heat transfer member 32 (lower substrate) are provided around the elastic vessel portion 70e. Specifically, the plate-like substrate 51a is provided on the upper surface side of the elastic vessel portion 70e, and the heat transfer member 32 is provided on the lower surface side of the elastic vessel portion 70e.

The plate-like substrate 51a is preferably a heat transfer member having thermal conductivity, and preferably uses a resin substrate having high thermal conductivity. Moreover, a concave PCR amplification vessel 52e (concave portion) may be provided in the plate-like substrate 51a. Thereby, capacity of the elastic vessel portion 70e can be defined. Moreover, since the PCR amplification vessel 52e does not penetrate the plate-like substrate 51a, the elastic vessel portion 70e is not exposed to room temperature, and heat keeping effects can be also obtained. The size of the PCR amplification vessel 52e may be appropriately designed considering the volume of the elastic vessel portion 70e.

For example, as a material of the plate-like substrate 51a, a resin substrate such as an acrylic plate, polydimethylsiloxane (PDMS) or silicon rubber may be used. The acrylic plate is particularly preferable since the thermal conductivity is improved and the acrylic plate has elasticity of an extent capable of forming a concave portion. The thickness of the plate-like substrate 51a may be the thickness of an extent which forms the PCR amplification vessel 52e. The thinner the thickness of the plate-like substrate 51a below the bottom surface of the PCR amplification vessel 52e is, the smaller the thermal resistance is, and thus, it is more preferable that the thickness be thin. The thermal resistance can be controlled by controlling the thermal conductivity and the thickness of the plate-like substrate 51a.

Moreover, in order to heat the upper surface side of the elastic vessel portion 70e, the heater 300 may be provided at a position opposite to the elastic vessel portion 70e while interposing the plate-like substrate 51a. The area of the heater 300 is preferably larger than the area of the elastic vessel portion 70e when seen in a plan view. Thereby, heat, which is generated from the heater 300 provided immediately below the elastic vessel portion 70e, is conducted to the plate-like substrate 51a, and the entire upper surface side of the elastic vessel portion 70e is heated. For example, as the heater 300, a heater, which uses a heating wire such as an iron chrome wire or a nichrome wire (a nickel-chrome wire), may be used. In addition, a sheet-like heater may be used in which a heat generating resistor such as nickel alloy is interposed by insulating materials configured of resin sheets such as polyimide sheets.

Metal materials such as copper, silver, aluminum may be used for the heat transfer member 32. When copper is used, in order to prevent oxidation, gold plating may be performed on a contact surface between the elastic vessel portion 70e and the heat transfer member 32. Thereby, the contact thermal resistance in the contact surface between the elastic vessel portion 70e and the heat transfer member 32 can be decreased. It is preferable that the area of the heat transfer member 32 be larger than the area of the elastic vessel portion 70e when seen in a plan view. The heat transfer member 32 is provided immediately below the elastic vessel portion 70e, and thus, the heat generated from the heat transfer member 32 heats the entire lower surface side of the elastic vessel portion 70e. In the present exemplary embodiment, the heat transfer member 32 may be configured of a material having higher thermal conductivity than the thermal conductivity of the plate-like substrate 51a.

Referring to FIG. 5 again, the heating unit, which is included in a temperature control device of the microchip used in the present exemplary embodiment, will be described in detail below. Both of the peltier element 31 and the heater 300 are members which generate heat when power is input from the power source 31c.

The power source 31c can be controlled by the controller 15, and for example, the heater 300 may be controlled so as to be constantly heated to a predetermined temperature (for example, 90° C.). On the other hand, in the heat transfer member 32, the peltier element 31, which is a current-heat conversion element, is provided so as to abut the surface opposite to the surface on which the third film 51d is provided. A temperature sensor (not shown in the drawings) is provided on the surface of the heat transfer member 32 which contacts the third film 51d. Here, the temperature sensor and the peltier element 31 are connected to the power source 31c, and the peltier element 31 is configured so that the temperature of the element is controlled by the controller 15. That is, as programmed in advance by the controller 15, the controller receives feedback from the temperature sensor and controls the peltier element 31, and heat conduction is performed by generating heat or radiating heat. By using the present configuration, the peltier element 31 can perform heat collection or heat dispersion and is controlled so as to heat the elastic vessel portion 70e at a desired temperature through the heat transfer member 32. For example, the peltier element 31 may be controlled so as to heat the elastic vessel portion 70e at a first temperature (90° C. to 100° C.) and a second temperature (50° C. to 60° C.) which is lower than the first temperature.

Moreover, in the present exemplary embodiment, the configuration is shown in which the temperature control is performed automatically by the controller 15. However, the temperature controls of the peltier element 31 and the heater 300 may be manually performed respectively without providing the controller 15.

Moreover, in order to heat the lower surface side of the elastic vessel portion 70e, the peltier element 31 is preferably provided at the position opposite to the elastic vessel portion 70e while interposing the heat transfer member 32.

Figure 6:
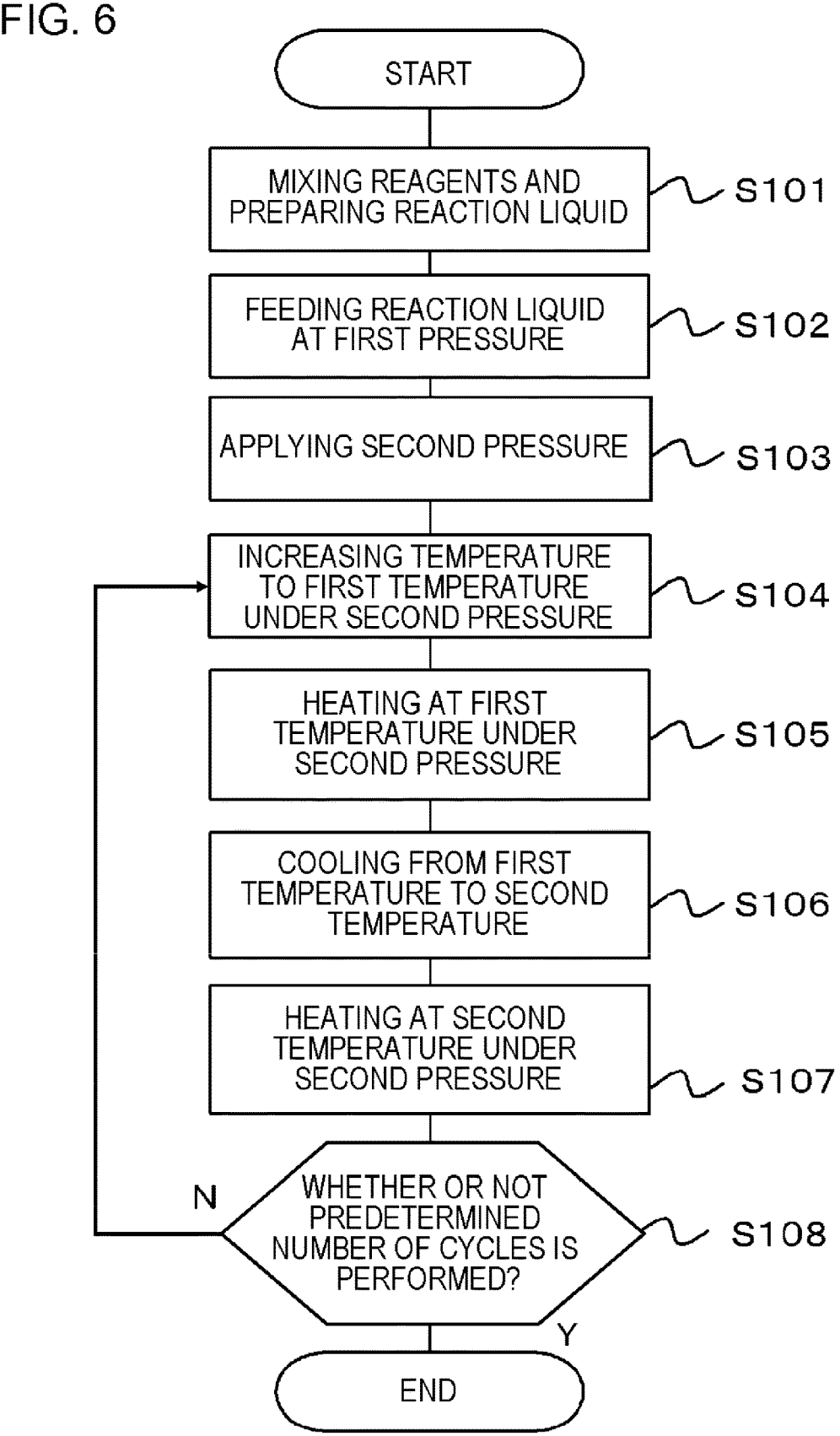
FIG. 6 is a flowchart which illustrates a sample heating method using the microchip according to the first exemplary embodiment.
Figure 7:
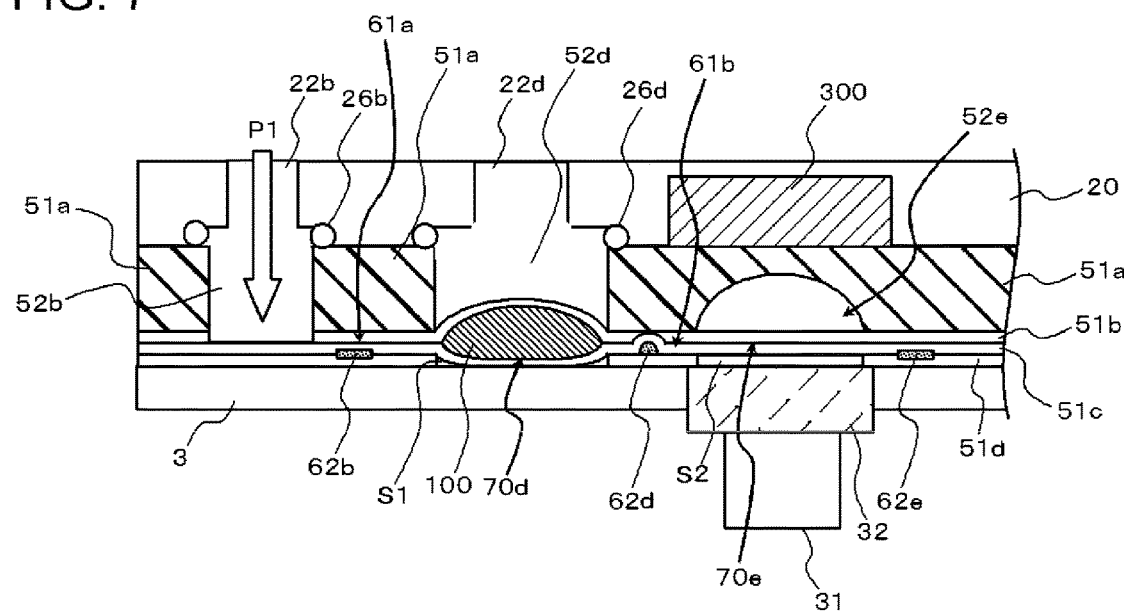
FIG. 7 is a cross-sectional view which illustrates the sample heating method using the microchip according to the first exemplary embodiment.
Figure 8:
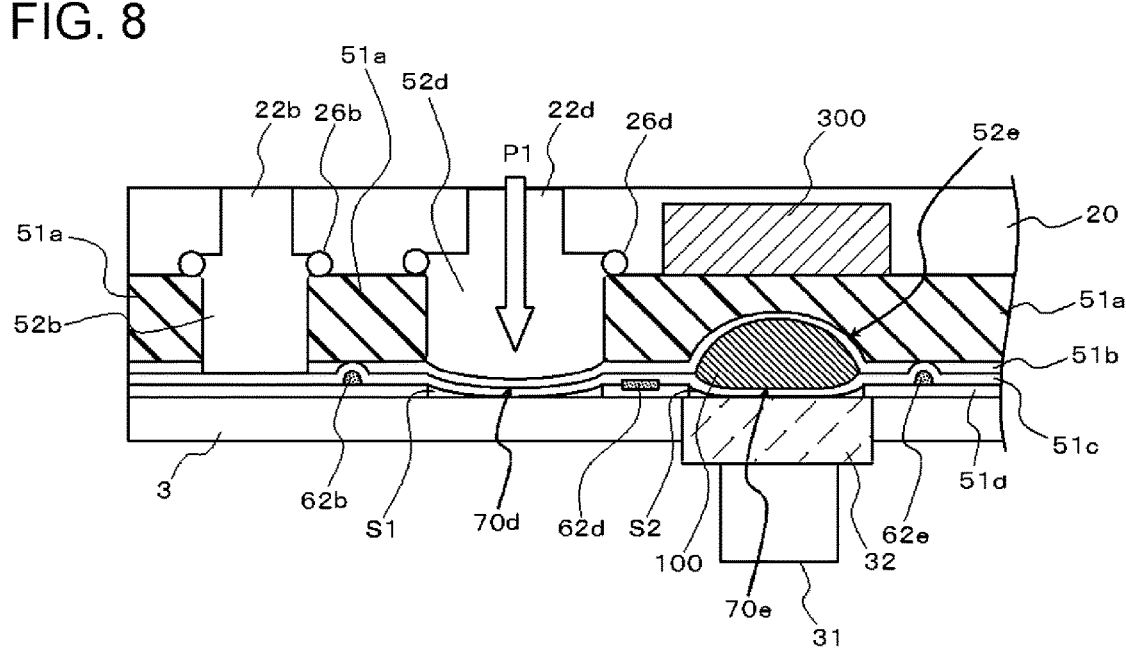
FIG. 8 is a cross-sectional view which illustrates the sample heating method using the microchip according to the first exemplary embodiment.
Figure 9:
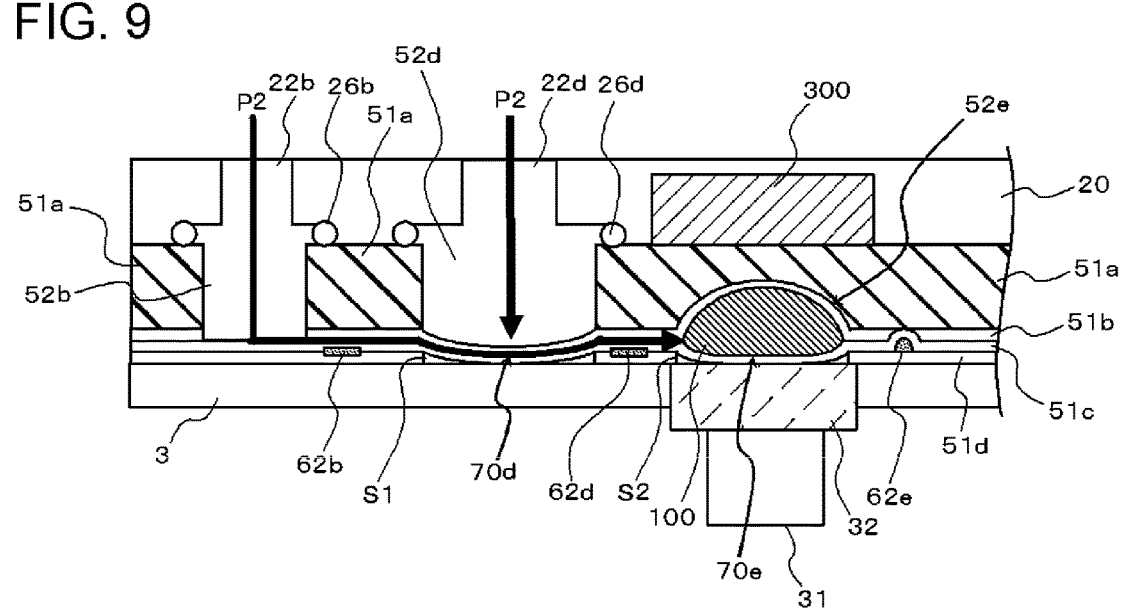
FIG. 9 is a cross-sectional view which illustrates the sample heating method using the microchip according to the first exemplary embodiment.

Subsequently, a sample heating method which uses the microchip of the present exemplary embodiment will be described with reference to FIGS. 6 to 9. FIG. 6 is a flowchart which illustrates the sample heating method which uses the microchip according to the present exemplary embodiment. Moreover, FIGS. 7 to 9 are views which illustrate the sample heating method which uses the microchip according to the present exemplary embodiment, and are cross-sectional views taken along line A-A in FIGS. 1 to 3. Hereinafter, a method, which automatically controls temperature and pressure using the controller 15 shown in FIGS. 3 and 5, will be described as an example.

First, a template DNA or reagent (primer, DNA polymerase, deoxynucleoside triphosphate, and buffer water solution), which becomes a test object, is filled in the reagent tank 52a, the reagent tank 52b, and the reagent tank 52c.

Subsequently, the controller 15 instructs operation commands which are programmed in advance, determined sequence operations are performed, a pressurizing medium (hereinafter, air as an example) is flowed inward from the shutter pressurizing hole 23d, and thus, the flow channel 61b is closed. Moreover, a pressurizing medium (hereinafter, air as an example) is sequentially flowed inward from the shutter pressurizing hole 23a, the shutter pressurizing hole 23b, and the shutter pressurizing hole 23c, and thus, the flow channel 61a is opened, the shutter flow channel 62a, the shutter flow channel 62b, and the shutter flow channel 62c are sequentially opened and closed.

Subsequently, a first pressure (P1, 180 kPa to 200 kPa as an example) is applied to the reagent tank 52a, the reagent tank 52b, and the reagent tank 52c, in which the template DNA or the reagent which becomes the test object is filled, from the pressurizing hole 22a, the pressurizing hole 22b, and the pressurizing hole 22c, and thus, sequentially, the sample and the reagent are fed to the elastic vessel portion 70d. The pressurizing medium is flowed into the shutter flow channel 62d, and thus, pressure is applied from the rear surface of the second film 51c, the second film 51c is bent, and the flow channel 61b is closed. As a result, as shown FIG. 7, the sample and the reagent, which are flowed into the elastic vessel portion 70d from the flow channel 61a, expand the elastic vessel portion 70d in a balloon shape, and are filled in the inner portion of the elastic vessel portion 70d. Thereby, the sample and the reagent are mixed in the elastic vessel portion 70d and a reaction liquid (liquid sample) 100 is prepared (S101).

Subsequently, the pressurizing medium is flowed into the shutter flow channel 62a, the shutter flow channel 62b, the shutter flow channel 62c, and the shutter flow channel 62e respectively, and thus, the second film 51c is bent, and the flow channel 61a and the flow channel 61c are closed. On the other hand, the shutter flow channel 62d is opened, and the flow channel 61b is opened. Moreover, the pressurizing medium is flowed from the pressurizing hole 22d to the mixing vessel 52d, and thus, the first pressure (P1) is applied to the elastic vessel portion 70d, and the reaction liquid 100 is fed to the elastic vessel portion 70e through the flow channel 61b (S102). As a result, the reaction liquid 100 expands the elastic vessel portion 70e in a balloon shape, and is filled in the inner portion of the elastic vessel portion 70e. At this time, a portion of the elastic vessel portion 70e is expanded upward and comes into press-contact with the PCR amplification vessel 52e provided on the plate-like substrate 51a. Moreover, a portion of the elastic vessel portion 70e is expanded downward and comes into press-contact with the heat transfer member 32 through the third film 51d (FIG. 8).

Subsequently, the shutter flow channel 62d is opened, and at least one of the shutter flow channel 62a, the shutter flow channel 62b, and the shutter flow channel 62c is opened in a state where the shutter flow channel 62e is closed. Moreover, the pressurizing medium is flowed from any one of the pressurizing hole 22a, the pressurizing hole 22b, and the pressurizing hole 22c which can feed liquid according to opening of the shutter flow channel, and a second pressure (P2) is applied to the inner portion of the elastic vessel portion 70e (S103). The second pressure may be constant or may be changed. However, it is preferable that the second pressure be constant. Specifically, the second pressure (P2) is equal to or more than 40 kPa, and thus, the contact thermal resistance can be decreased and be controlled so as to be constant. Moreover, the pressure is preferably equal to or more than saturated vapor pressure of solvent of the reaction liquid 100 in the heated temperature, and is more preferably equal to or more than the saturated vapor pressure in the heated maximum temperature. For example, in a case where the reaction liquid 100 is repeatedly heated at 97° C. and 53° C., when the solvent of the reaction liquid 100 is water, it is preferable that the water be pressurized at equal to or more than 100 kPa. Moreover, at this time, the pressure is applied with respect to the elastic vessel portion 70d through the mixing vessel 52d from the pressurizing hole 22d, and thus, the pressurizing medium can be led to the elastic vessel portion 70e without expanding the elastic vessel portion 70d too much. Thereby, a desired pressure can be applied to the elastic vessel portion 70e (FIG. 9).

Moreover, it is preferable that the first film 51b, which is expanded by pressurization, closely contact the PCR amplification vessel 52e of the plate-like substrate 51a. Moreover, it preferable that the expanded second film 51c closely contact the heat transfer member 32. Thereby, the entire elastic vessel portion 70e closely contacts the plate-like substrate 51a and the heat transfer member 32, and thus, the contact thermal resistance can be decreased. Moreover, the elastic vessel portion 70e closely contacts the plate-like substrate 51a and the heat transfer member 32, and thus, leakage of the solvent (water) from the elastic vessel portion 70e can be decreased.

In addition, the reaction liquid 100 is heated at the first temperature and the second temperature which is lower than the first temperature by controlling the peltier element 31 and the heater 300. In the present exemplary embodiment, the heater 300 can be controlled so as to generate heat at a constant temperature. On the other hand, the peltier element 31 can be controlled so that the reaction liquid 100 is heated by the reaction liquid 100 at the first temperature and the second temperature lower than the first temperature due to the heat generation of the peltier element 31. In the present exemplary embodiment, the thermal conductivity of the heat transfer member 32 is configured to be higher than the thermal conductivity of the plate-like substrate 51a. Moreover, the elastic vessel portion 70e is configured so that the contact thermal resistance is sufficiently decreased. Thereby, the heating temperature of the reaction liquid 100 can be accurately controlled even when the temperature is controlled by only the heat transfer member 32 having high thermal conductivity.

Specifically, a heating process is performed as follows. First, in a state where the second pressure (P2) is applied to the elastic vessel portion 70e, the inner portion of the elastic vessel portion 70e is increased to the first temperature (for example, 90° C. to 100° C., and 97° C. as an example) by the peltier element 31 and the heater 300 (S104), and the reaction liquid 100 is heated at the first temperature under the second pressure (S105). Subsequently, after a predetermined time is elapsed, the inner portion is cooled from the first temperature to the second temperature (for example, 50° C. to 60° C., and 53° C. as an example) by controlling the peltier element 31 (S106), and the reaction liquid 100 is heated for a predetermined time at the second temperature under the second pressure (S107).

In addition, according to programs which are installed in advance, it is determined whether or not a predetermined number of cycles is performed on a computer (not shown in the drawings) (S108). When the predetermined number of cycles is not performed (S108N), the reaction liquid is increased to the first temperature again, and the heating of the reaction liquid 100 at the first temperature and the second temperature is repeated under the second pressure. On the other hand, when the predetermined number of cycles (for example, 30 cycles) is performed (S108Y), the heating stops, the reaction liquid is cooled to room temperature, and like, and thus, the reaction ends. In this way, a desired DNA can be amplified.

By mounting an analyzer in the elastic vessel portion 70e, the amplified DNA can be analyzed in a state where the DNA is put in the elastic vessel portion 70e. In addition, the reaction liquid 100, which is put in the elastic vessel portion 70e, is discharged from the flow channel 61c, and a desired analysis may be performed. When the reaction liquid is discharged from the elastic vessel portion 70e, a minute through hole which penetrates the plate-like substrate 51a and the heater 300 may be provided within a range which does not hinder the effects of the present exemplary embodiment. Thereby, pressure can be applied to the elastic vessel portion 70e from the PCR amplification vessel 52e, and the reaction liquid 100 can be discharged to the flow channel 61c.

Next, advantageous operation effects of the present exemplary embodiment will be explained.

In the present exemplary embodiment, the reaction liquid 100 is heated while the pressure is applied to the inner portion of the elastic vessel portion 70e in which the reaction liquid 100 is put. Thereby, it is possible to prevent the solvent in the reaction liquid 100 from being vaporized and permeating the film-like elastic member which configures the elastic vessel portion 70e. Therefore, change of the reaction environment is minimized, the DNA amplification reaction is effectively advanced by the heating, or liquid feeding after the heating can be smoothly performed.

A mechanism, in which the solvent in the reaction liquid disappears from the sealed elastic vessel portion, is considered as follows. The solvent in the reaction liquid in the inner portion of the sealed elastic vessel portion is vaporized until reaching the saturated vapor pressure. The vaporized gas easily permeates the film-like elastic member which configures the elastic vessel portion. Here, when the inner portion of the elastic vessel portion is heated, the saturated vapor pressure is increased with an increase of the temperature. Thereby, vaporization of the solvent is promoted along with heating of the solvent, the vaporized gas permeates the film-like elastic member, and thus, it is considered that the solvent in the reaction liquid disappears.

On the other hand, in the method of the present exemplary embodiment, since the reaction liquid 100 is pressurized, the phenomenon, in which the solvent in the reaction liquid is vaporized until reaching the saturated vapor pressure, can be suppressed. Thereby, disappearance of the solvent from the elastic vessel portion 70e can be prevented.

Moreover, considering the above-described mechanism, in the present exemplary embodiment, it is preferable that the reaction liquid 100 be pressurized by higher pressure than the saturated vapor pressure of the solvent in the heating temperature of the reaction liquid 100. Moreover, it is preferable that the reaction liquid 100 be pressurized by higher pressure than the saturated vapor pressure of the solvent in the first temperature which is the maximum temperature in the heating temperature of the reaction liquid 100. Thereby, the vaporization of the solvent in the reaction liquid can be more securely suppressed. Moreover, since air bubbles do not occur in the inner portion of the elastic vessel portion 70e, the heat transfer can be uniformly maintained.

Moreover, in the present exemplary embodiment, by applying pressure to the inner portion of the elastic vessel portion 70e, the second film 51c and the third film 51d are expanded, and the elastic vessel portion 70e can closely contact the plate-like substrate 51a heated by the heater 300 and the heat transfer member 32. Thereby, dispersion of the gas which permeates the second film 51c and the third film 51d can be blocked by the plate-like substrate 51a or the heat transfer member 32. Therefore, disappearance of the solvent from the elastic vessel portion 70e can be more securely suppressed.

In addition, in the present exemplary embodiment, by applying pressure to the inner portion of the elastic vessel portion 70e, the second film 51c and the third film 51d can be expanded, the contact between the elastic vessel portion and the heat transfer member 32 is improved, and thus, the contact thermal resistance can be decreased. Moreover, by further applying pressure to the inner portion of the elastic vessel portion 70e in the state where the elastic vessel portion 70e closely contacts the heat transfer member 32, the contact thermal resistance can be constantly controlled. This is because contact thermal conductance (a reciprocal number of the contact thermal resistance) with respect to the contact pressure is increased in proportion to approximately the power of 0.6 of the contact pressure. For example, in the configuration of the present exemplary embodiment, since the pressure equal to or more than 40 kPa is applied, the contact thermal resistance becomes substantially constant. Thereby, it is possible to prevent the heat emitted from the peltier element 31 from being decreased due to resistances of air or the film which configures the elastic vessel portion 70e. Therefore, the reaction liquid 100 can be heated by the heat which is controlled by a desired temperature.

Moreover, in the present exemplary embodiment, in order to perform the amplification reaction of DNA, it is necessary to repeatedly heat according to two different temperatures in which the temperature difference is 30° C. to 40° C. In order to effectively perform the amplification reaction, a more strict temperature control is needed. The elastic vessel portion disclosed in Patent Document 1 has the structure in which the upper surface side is opened to the atmosphere while the lower surface side is heated. Thereby, the temperature of the lower surface side of the elastic vessel portion is controlled by the heater. On the other hand, the upper surface side is exposed to room temperature. In the sample having a very small amount of around several microliters, since the thermal capacity is small, the sample is easily cooled while the sample is easily warm. Therefore, in the upper surface and the lower surface of the elastic vessel portion, the temperature difference easily occurs, and thus, it is difficult to heat the reaction liquid at the objective temperature.

Thus, in the present exemplary embodiment, the plate-like substrate 51a is provided on the upper portion of the elastic vessel portion 70e, and the elastic vessel portion 70e is heated in the state where pressure is applied to the inner portion of the elastic vessel portion 70e through the flow channel 61b and the vessel portion closely contacts the plate-like substrate 51a. Thereby, the contact thermal resistance can also be decreased on the upper portion of the elastic vessel portion 70e. Moreover, it is possible to prevent the upper portion of the elastic vessel portion 70e from being cooled due to room temperature. Therefore, a more precise temperature control is possible.

Moreover, in the present exemplary embodiment, the plate-like substrate 51a is set to the heat transfer member having thermal conductivity, and the heater 300 is provided on the upper portion. Thereby, the elastic vessel portion 70e can be heated from the upper portion in the state where pressure is applied to the inner portion of the elastic vessel portion 70e and the vessel portion closely contacts the plate-like substrate 51a. Therefore, since heat radiation of the upper portion of the elastic vessel portion 70e can be prevented, a more precise temperature control is possible, and it is possible to effectively perform temperature cycles of 90° C. to 100° C. and 50° C. to 60° C. in the PCR amplification reaction.

Moreover, in the present exemplary embodiment, the sizes of the heater 300 and the plate-like substrate 51a are configured so as to be larger than the size of the elastic vessel portion 70e when seen in a plan view. The size of the heat transfer member 32 is also provided so as to be larger than the size of the elastic vessel portion 70e when seen in a plan view. Therefore, the elastic vessel portion 70e can be heated from the periphery, the reaction liquid 100 put in the elastic vessel portion 70e can be accurately heated to the objective temperature, and the DNA amplification reaction can be effectively performed.

Moreover, in the present exemplary embodiment, since the elastic vessel portion 70e can be heated in the state where the vessel portion closely contacts the plate-like substrate 51a, the vaporized solvent is difficult to go through the film which configures the elastic vessel portion 70e. Therefore, according to the configuration of the present exemplary embodiment, it is possible to securely suppress the vaporized solvent from being flowed out the vessel portion.

Second Exemplary Embodiment

Figure 10:
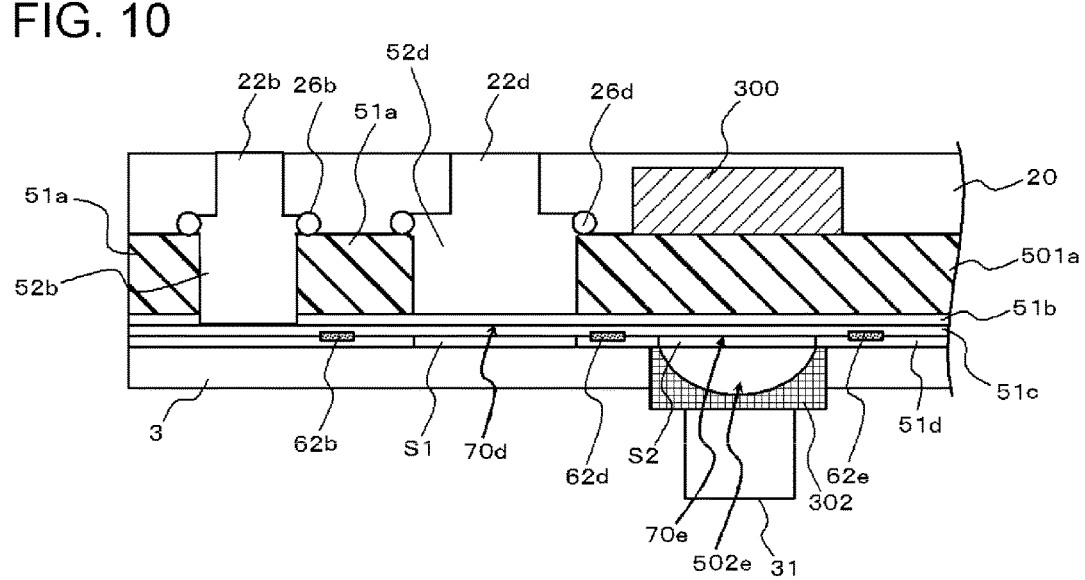
FIG. 10 is another example of the cross-sectional view taken along line A-A of the microchip shown in FIGS. 1 to 3.

FIG. 10 is a cross-sectional view showing a microchip which is used in the present exemplary embodiment. FIG. 10 is an example of the cross-sectional view taken along line A-A of the microchip shown in FIGS. 1 to 3. FIG. 10 shows the state before the sample is filled in the reagent tank 52a, the reagent tank 52b, the reagent tank 52c, the elastic vessel portion 70d, and the elastic vessel portion 70e. This microchip is different from the microchip described in the first exemplary embodiment only in that a plate-like substrate 501a, on which the concave PCR amplification vessel 52e is not formed, is used and a heat transfer member 302 in which a concave PCR amplification vessel 502e (concave portion) is formed on the heat transfer member 32 of the elastic vessel portion 70e is used, and other configurations are the same as the configurations of the microchip used in the first exemplary embodiment. In the present exemplary embodiment, only matters different from the first exemplary embodiment will be described, and the configurations similar to the first exemplary embodiment will not be repeated.

As shown in FIG. 10, in the microchip used in the present exemplary embodiment, the plate-like substrate 501a is provided on the upper surface side of the elastic vessel portion 70e.

On the other hand, the heat transfer member 302 is provided on the lower surface side of the elastic vessel portion 70e. In the heat transfer member 302, the concave PCR amplification vessel 502e, which can store the expanded elastic vessel portion 70e, is provided. The dimensions of the PCR amplification vessel 502e can be designed according to the capacity of the elastic vessel portion 70e.

Moreover, the top view of the second film 51c is similar to FIG. 1, the top view of the plate-like substrate 501a is similar to FIG. 2, and the bottom view of the cover 20 is similar to FIG. 3.

Figure 11:
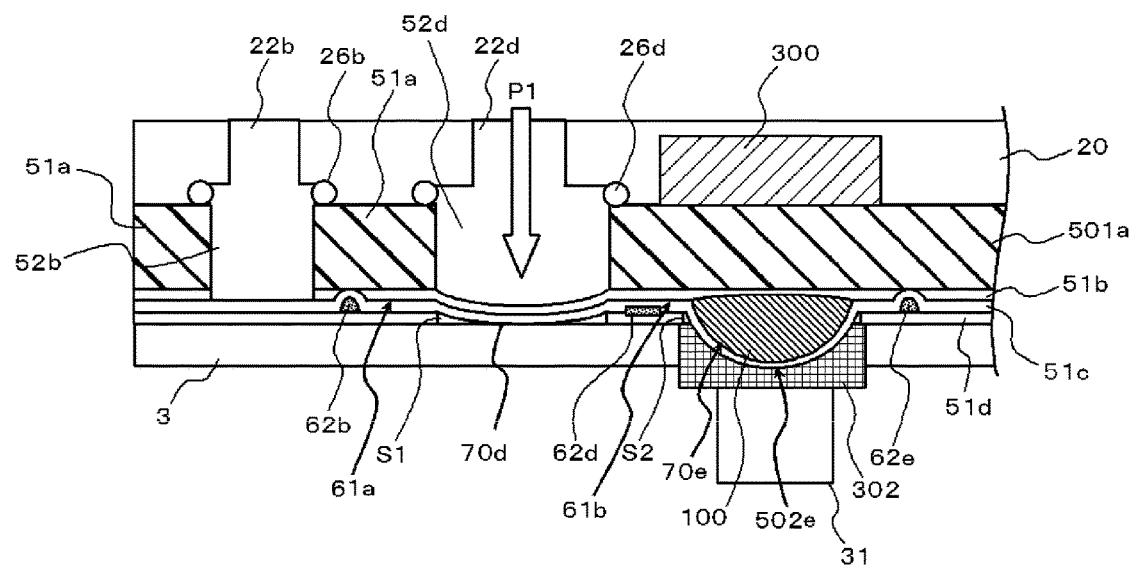
FIG. 11 is a cross-sectional view which illustrates a sample heating method using the microchip according to the second exemplary embodiment.
Figure 12:
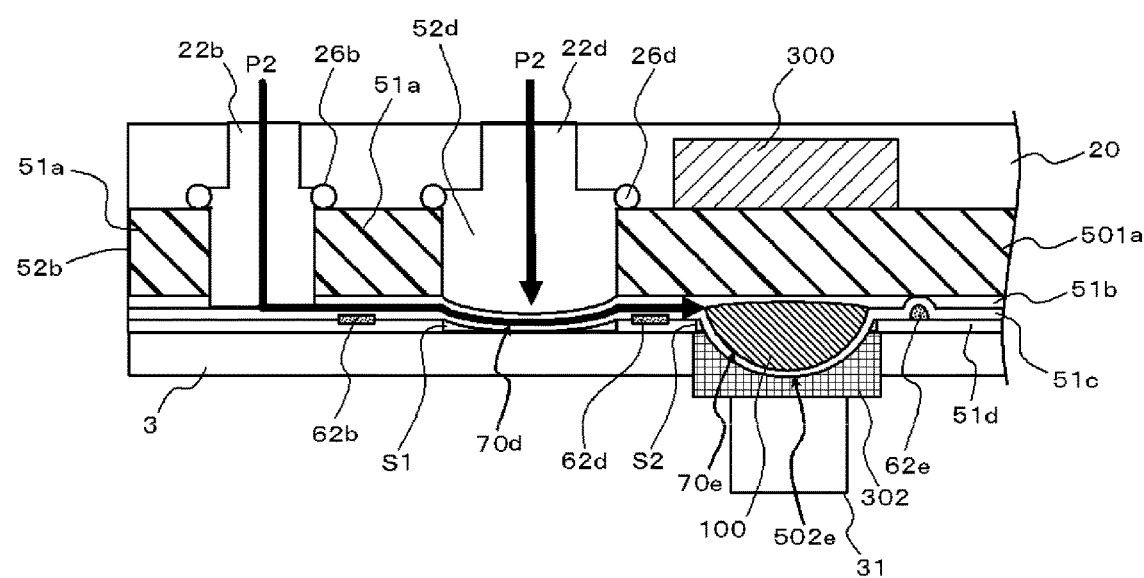
FIG. 12 is a cross-sectional view which illustrates the sample heating method using the microchip according to the second exemplary embodiment.
Figure 13:
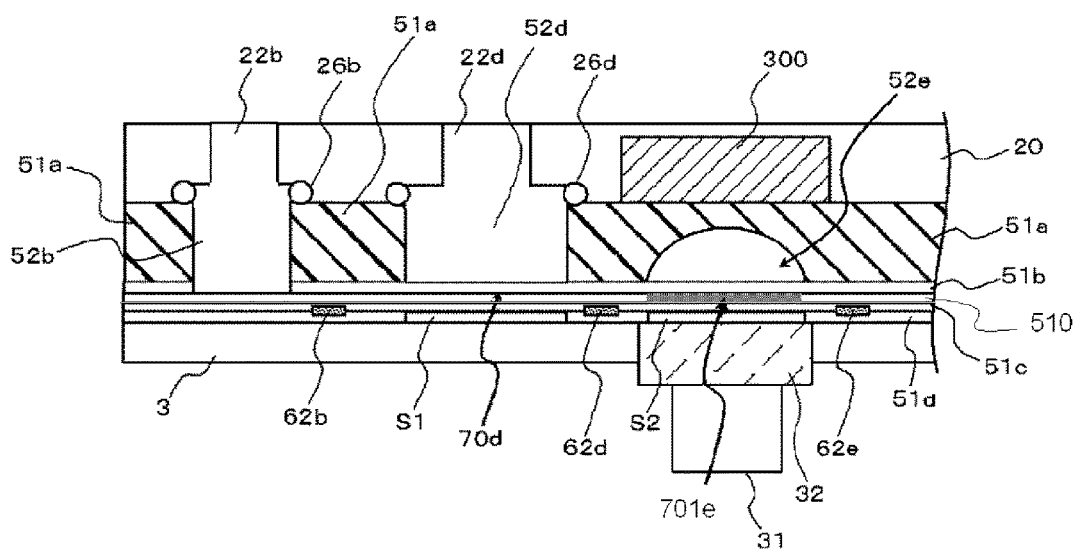
FIG. 13 is a modified example of the microchip according to the first exemplary embodiment.

Next, a sample heating method which uses the microchip of the present exemplary embodiment will be described with reference to FIGS. 11 and 12. The sample heating method of the present exemplary embodiment may also be performed according to the flowchart shown in FIG. 6. FIGS. 11 and 12 are cross-sectional views taken along line A-A in FIGS. 1 to 3 which illustrate the sample heating method which uses the microchip according to the present exemplary embodiment.

First, as described in the first exemplary embodiment, the sample and the reagent are mixed in the elastic vessel portion 70d and a reaction liquid (liquid sample) 100 are prepared (S101 in FIG. 6), and the reaction liquid 100 is fed to the elastic vessel portion 70e through the flow channel 61b (S102 in FIG. 6). As a result, the reaction liquid 100 expands the elastic vessel portion 70e in a balloon shape, and is filled in the inner portion of the elastic vessel portion 70e. At this time, a portion of the elastic vessel portion 70e is expanded upward and comes into press-contact with the plate-like substrate 51a. Moreover, a portion of the elastic vessel portion 70e is expanded downward and is put in the concave PCR amplification vessel 502e which is formed on the heat transfer member 302 (FIG. 11).

Subsequently, as described in the first exemplary embodiment, the second pressure (P2) is applied to arbitrary reagent tanks 52a, 52b, and 52c and the mixing vessel 52d (S103 in FIG. 6), and a desired pressure is applied to the elastic vessel portion 70e (FIG. 12). At this time, the second film 51c, which is expanded by the pressurization, closely contacts the heat transfer member 302, and the elastic vessel portion 70e is put in the PCR amplification vessel 502e. On the other hand, the expanded first film 51b closely contacts the plate-like substrate 501a. Thereby, the entire elastic vessel portion 70e closely contacts the plate-like substrate 501a and the heat transfer member 302, and the capacity of the elastic vessel portion 70e is limited by the PCR amplification vessel 502e. Moreover, since the lower surface side of the elastic vessel portion 70e is heated by the heat transfer member 302, the reaction liquid 100 in the elastic vessel portion 70e can be controlled at a predetermined temperature. In addition, since the plate-like substrate 501a is set to the heat transfer member, the heat from the heater 300 is conducted to the plate-like substrate 501a, and the upper surface side of the elastic vessel portion 70e is also heated.

Thereafter, as described in the first exemplary embodiment, the heating at the first temperature and the second temperature is performed by a predetermined number of cycles, and the DNA is amplified (S104 to S108 in FIG. 6).

Also in the configuration of the present exemplary embodiment, advantageous effects similar to the first exemplary embodiment can be obtained. However, since the reaction liquid 100 is put in the inner portion of the heat transfer member 302 which can be heated at two different temperatures, in the present exemplary embodiment, there is an advantage in that the temperature of the reaction liquid 100 can be more effectively controlled.

As described above, exemplary embodiments of the present invention are described with reference to the drawings. However, the exemplary embodiments exemplify the present invention, and various configurations other than the above-described may be adopted.

In the present exemplary embodiment, for example, the configuration, in which the concave PCR amplification vessel is provided in either the plate-like substrate or the heater, is described by an example. However, concave portions are provided in both the plate-like substrate and the heat transfer member, and the PCR amplification vessels may be configured by the concave portions.

Moreover, in the present exemplary embodiment, the example is described in which the heat transfer member provided on the lower surface side of the elastic vessel portion can be controlled at two different temperatures and the temperature of the heater provided on the upper surface side is maintained to a constant temperature. However, the upper surface side of the elastic vessel portion may be heated by abutting the peltier element to the elastic vessel portion and controlling at an arbitrary temperature. In this case, the upper surface side of the elastic vessel portion may be heated by the peltier element through a conduction member made of a metal. Moreover, the lower surface side of the elastic vessel portion may be heated by the heater through the heat transfer member such as a resin substrate in stead of the heat transfer member and the peltier element. Moreover, the heat transfer member or the plate-like substrate is not necessarily needed, and the upper portion and the lower portion of the elastic vessel portion may be directly heated by the heater or the peltier element. That is, in the present invention, any configuration may be adopted if it can heat the upper surface side and the lower surface side of the elastic vessel portion.

Moreover, in the present exemplary embodiment, the example is described in which pressure is applied to the inner portion of the vessel portion through the flow channel. However, in other examples, a configuration may be adopted in which pressure is applied from the outer portion of the elastic vessel portion through the pressurizing hole or the like, and thus, the pressure operates to the liquid sample in the elastic vessel portion. Specifically, for example, similar to Patent Document 1, the upper portion of the elastic vessel portion is opened by providing the through hole in the plate-like substrate, the pressure is applied from the outside of the elastic vessel portion, and the liquid sample put in the elastic vessel portion may be heated by the heater installed on the lower surface side of the elastic vessel portion while the pressure is applied to the inner portion of the elastic vessel portion. Also according to this configuration, since the liquid sample is pressurized, the phenomenon, in which the solvent in the liquid sample is vaporized until reaching the saturated vapor pressure, can be suppressed. Thereby, disappearance of the solvent from the elastic vessel portion can be prevented.

Moreover, the present exemplary embodiment is described using the drawings in which the volume of the elastic vessel portion, in which the sample is not filled, is substantially zero. However, even when a small amount of gas or air bubble is contained in the elastic vessel portion of the initial state in which the sample is not filled, it is permitted if the amount is a very small. This is because a very small amount of gas or air bubble can permeate from the film when pressure is applied. Therefore, for example, in the present invention, a modification example shown in FIG. 13 may be adopted. In the modification example shown in FIG. 13, in addition to the example shown in FIG. 4, a fourth film 510 is further provided between the second film 51c and the third film 51d. Similar to the second film 51c or the third film 51d, the fourth film 510 is also configured of a film-like elastic member. In the fourth film 510, a space 701e is formed immediately below the PCR amplification vessel 52e, and this space 701e becomes an elastic vessel portion. Also in the example of FIG. 10, similarly, the fourth film 510 may be provided, and instead of the elastic vessel portion 52e, the elastic vessel portion of the space 701e may be adopted. The space 701e also functions similarly to the elastic vessel portion 52e, and as described in the exemplary embodiments, the sample is filled in the space 701e, and the cycle shown in FIG. 6 is repeated, and thus, the PCR amplification may be performed. Also in Modification Example, advantageous effects of the present invention can be obtained.

This application claims priority based on Japanese Patent Application No. 2010-284217, filed Dec. 21, 2010.

What is claimed is:

1. A sample heating method which uses a microchip, comprising the steps of:
   wherein the microchip includes: a vessel portion in which at least a portion is configured of an elastic member; and a flow channel which leads a liquid sample to the vessel portion,
   heating the liquid sample while applying pressure to the liquid sample from outside of the vessel portion,
   wherein the microchip further includes an expansion limiting member which is provided around the vessel portion and limits expansion of the elastic member,
   wherein at least a portion of the expansion limiting member is configured of either a heat generation member or a heat transfer member, and
   wherein the liquid sample is heated in a state where pressure is applied with respect to the inner portion of the vessel portion and thus, the vessel portion contacts either the heat generation member or the heat transfer member of the expansion limiting member.

2. The sample heating method according to claim 1, wherein the liquid sample is heated while pressure is applied with respect to the inner portion of the vessel portion through the flow channel.

3. The sample heating method according to claim 1, wherein the expansion limiting member is configured of either the heat generation member or the heat transfer member, and the liquid sample is heated in a state where pressure is applied with respect to the inner portion of the vessel portion through the flow channel, and thus, the entire vessel portion contacts the expansion limiting member.

4. The sample heating method according to claim 1, wherein a concave portion is provided in the expansion limiting member, and the liquid sample is heated in a state where at least a portion of the expanded vessel portion contacts the concave portion.

5. The sample heating method according to claim 1, wherein the expansion limiting member includes an upper substrate provided over an upper surface side of the vessel portion and a lower substrate provided over a lower surface side of the vessel portion,
   wherein at least one of the upper substrate and the lower substrate is configured of either the heat generation member or the heat transfer member, and the liquid sample is heated in a state where the vessel portion contacts the upper substrate or the lower substrate which configures either the heat generation member or the heat transfer member.

6. The sample heating method according to claim 5, wherein both of the upper substrate and the lower substrate are configured of either the heat generation member or the heat transfer member, and the liquid sample is heated in a state where the upper surface side of the vessel portion closely contacts the upper substrate and the lower surface side of the vessel portion closely contacts the lower substrate.

7. The sample heating method according to claim 6, wherein the upper substrate is configured of a first heat transfer member, the lower substrate is configured of a second heat transfer member having higher thermal conductivity than that of the first heat transfer member, and
wherein the lower substrate is controlled so as to heat the liquid sample at a first temperature and a second temperature lower than the first temperature, the upper member is controlled so as to heat the liquid sample at a constant temperature, and the liquid sample is alternately heated at the first temperature and the second temperature.

8. The sample heating method according to claim 5, wherein a concave portion is provided over at least one of the upper substrate and the lower substrate, and at least a portion of the expanded vessel portion contacts the concave portion and thus, the liquid sample is heated.

9. The sample heating method according to claim 1, wherein the microchip includes:
a first film-like elastic member; and
a second film-like elastic member which is stacked so as to contact the first elastic member,
wherein the first elastic member and the second elastic member contact each other around the vessel portion and the flow channel, and thus, the flow channel and the vessel portion are formed respectively in a gap between the first elastic member and the second elastic member.

10. The sample heating method according to claim 1, wherein the sample includes at least DNA, and an amplification reaction (Polymerase Chain Reaction (PCR)) of DNA is performed by heating the sample.

* * * * *